(12) United States Patent
Mizoguchi et al.

(10) Patent No.: US 11,467,392 B2
(45) Date of Patent: Oct. 11, 2022

(54) ENDOSCOPE PROCESSOR, DISPLAY SETTING METHOD, COMPUTER-READABLE RECORDING MEDIUM, AND ENDOSCOPE SYSTEM

(71) Applicant: OLYMPUS CORPORATION, Tokyo (JP)

(72) Inventors: Masakazu Mizoguchi, Hachioji (JP); Yasushi Namii, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/109,530

(22) Filed: Dec. 2, 2020

(65) Prior Publication Data

US 2021/0096351 A1    Apr. 1, 2021

Related U.S. Application Data

(63) Continuation of application No. PCT/JP2019/022229, filed on Jun. 4, 2019.

(30) Foreign Application Priority Data

Jun. 4, 2018 (JP) .............................. JP2018-107226

(51) Int. Cl.
*G02B 23/24* (2006.01)
*G02B 23/00* (2006.01)
(Continued)

(52) U.S. Cl.
CPC ....... *G02B 23/243* (2013.01); *G02B 23/2461* (2013.01); *G02B 23/2476* (2013.01); *H04N 5/2253* (2013.01); *H04N 2005/2255* (2013.01)

(58) Field of Classification Search
USPC ........................................ 348/45, 42, 51, 47
See application file for complete search history.

(56) References Cited

U.S. PATENT DOCUMENTS

| 2001/0033327 A1 | 10/2001 | Uomori et al. |
| 2002/0024592 A1 | 2/2002 | Uomori et al. |
| (Continued) | | |

FOREIGN PATENT DOCUMENTS

| JP | H09-121370 A | 5/1997 |
| JP | 2004-007396 A | 1/2004 |
| (Continued) | | |

OTHER PUBLICATIONS

International Search Report dated Aug. 27, 2019 issued in PCT/JP2019/022229.

*Primary Examiner* — Daquan Zhao
(74) *Attorney, Agent, or Firm* — Scully, Scott, Murphy & Presser, P.C.

(57) ABSTRACT

An endoscope processor includes: an acquisition circuit configured to acquire display size information on a display that is connected to the endoscope processor; a display condition setting circuit configured to set, according to the acquired display size information and properties of an imager of an endoscope that is connected to the endoscope processor, a monitor shift value representing an amount of shift between a first image and a second image corresponding to first image data and second image data, respectively, the first image data and the second image data each having parallax with respect to a same subject; and an image processor configured to shift the first image and the second image to generate display image data to be output to the display using the set monitor shift value.

10 Claims, 12 Drawing Sheets

(51) Int. Cl.
  *G02B 25/00*    (2006.01)
  *G02B 21/00*    (2006.01)
  *G02B 26/00*    (2006.01)
  *H04N 5/225*    (2006.01)

(56) References Cited

U.S. PATENT DOCUMENTS

| | | |
|---|---|---|
| 2005/0089212 A1 | 4/2005 | Mashitani et al. |
| 2011/0090217 A1 | 4/2011 | Mashitani et al. |
| 2011/0102427 A1 | 5/2011 | Mashitani et al. |
| 2011/0254925 A1* | 10/2011 | Ushiki ................ H04N 13/139 348/46 |
| 2013/0315558 A1 | 11/2013 | Nakamura |
| 2016/0029011 A1* | 1/2016 | Mizoguchi ........... H04N 13/204 348/45 |
| 2017/0251911 A1 | 9/2017 | Ito |

FOREIGN PATENT DOCUMENTS

| | | |
|---|---|---|
| JP | 2006-055291 A | 3/2006 |
| JP | 2016-046780 A | 4/2016 |
| WO | WO 2012/105121 A1 | 8/2012 |
| WO | WO 2017/038774 A1 | 3/2017 |
| WO | WO 2017/104192 A1 | 6/2017 |

\* cited by examiner

| ENDOSCOPE TYPE / MONITOR SIZE | MODEL A | MODEL B | MODEL C | MODEL D |
|---|---|---|---|---|
| 24 | | | | |
| 32 | | | | |
| 42 | | | | |
| 50 | | | | |
| 55 | | | | |

ENDOSCOPE PROCESSOR, DISPLAY SETTING METHOD, COMPUTER-READABLE RECORDING MEDIUM, AND ENDOSCOPE SYSTEM

CROSS-REFERENCE TO RELATED APPLICATIONS

This application is a continuation of PCT international application No. PCT/JP2019/022229 filed on Jun. 4, 2019, which designates the United States, incorporated herein by reference, and which claims the benefit of priority from Japanese Patent Application No. 2018-107226, filed on Jun. 4, 2018, incorporated herein by reference.

BACKGROUND

1. Technical Field

The disclosure relates to an endoscope processor, a display setting method, a computer-readable recording medium, and an endoscope system.

2. Related Art

In the medical field in recent years, there has been a demand to observe a subject to be observed using stereoscopic images in order to smooth diagnosis and examination. A technique for the demand has been known, where an endoscope system including an endoscope and a processing device (endoscope processor) generates a parallax image from two sets of image data for the left eye and the right eye each having parallax and displays a stereoscopic image (for example, refer to Japanese Laid-open Patent Publication No. 2016-46780). According to Japanese Laid-open Patent Publication No. 2016-46780, an endoscope acquires sets of in-vivo image data for the left eye and the right eye of a subject and an endoscope processor generates a parallax image from the two sets of image data and stereoscopically displays an in-vivo image of the subject. Furthermore, According to Japanese Laid-open Patent Publication No. 2016-46780, based on information on a display environment in which an image stored in a storage device is displayed and information on a display device, it is determines whether there is a difference between the display environment and a screen size and, when there is a difference, a shift value between the right-eye image and the left-eye image are corrected (alignment correction).

SUMMARY

In some embodiments, an endoscope processor includes: an acquisition circuit configured to acquire display size information on a display that is connected to the endoscope processor; a display condition setting circuit configured to set, according to the acquired display size information and properties of an imager of an endoscope that is connected to the endoscope processor, a monitor shift value representing an amount of shift between a first image and a second image corresponding to first image data and second image data, respectively, the first image data and the second image data each having parallax with respect to a same subject; and an image processor configured to shift the first image and the second image to generate display image data to be output to the display using the set monitor shift value.

In some embodiments, provided is a display setting method performed by an endoscope processor. The method includes: acquiring display size information on a display that is connected to the endoscope processor; according to the acquired display size information and properties of an imager of an endoscope that is connected to the endoscope processor, setting a monitor shift value representing an amount of shift between a first image and a second image corresponding to first image data and second image data, respectively, the first image data and the second image data each having parallax with respect to a same subject; and shifting the first image and the second image to generate display image data to be output to the display using the set monitor shift value.

In some embodiments, provided is a non-transitory computer-readable recording medium with an executable program stored thereon. The program causes an endoscope processor to execute: acquiring display size information on a display that is connected to the endoscope processor; according to the acquired display size information and properties of an imager of an endoscope that is connected to the endoscope processor, setting a monitor shift value representing an amount of shift between a first image and a second image corresponding to first image data and second image data, respectively, the first image data and the second image data each having parallax with respect to a same subject; and shifting the first image and the second image to generate display image data to be output to the display using the set monitor shift value.

In some embodiments, an endoscope system includes: an endoscope configured to acquire first image data and second image data each having parallax with respect to a same subject; a display configured to display an display image corresponding to display image data; and an endoscope processor configured to generate the display image data and output the generated display image data to the display, the endoscope processor including: an acquisition circuit configured to acquire display size information on the display; a display condition setting circuit configured to set, according to the acquired display size information and properties of an imager of an endoscope that is connected to the endoscope processor, a monitor shift value representing an amount of shift between a first image and a second image corresponding to the first image data and the second image data, respectively; and an image processor configured to shift the first image and the second image to generate the display image data to be output to the display using the set monitor shift value.

The above and other features, advantages and technical and industrial significance of this invention will be better understood by reading the following detailed description of presently preferred embodiments of the disclosure, when considered in connection with the accompanying drawings.

DETAILED DESCRIPTION

Modes for carrying out the disclosure ("embodiments" below) will be described below. In the embodiments, medical endoscope systems that capture and display in-vivo images of a subject, such as a patient, will be described as examples of a system including an endoscope processor according to the disclosure. The embodiments do not limit the disclosure. Furthermore, in the illustration of the drawings, the same components are denoted with the same reference numbers and described.

First Embodiment

Figure 1:
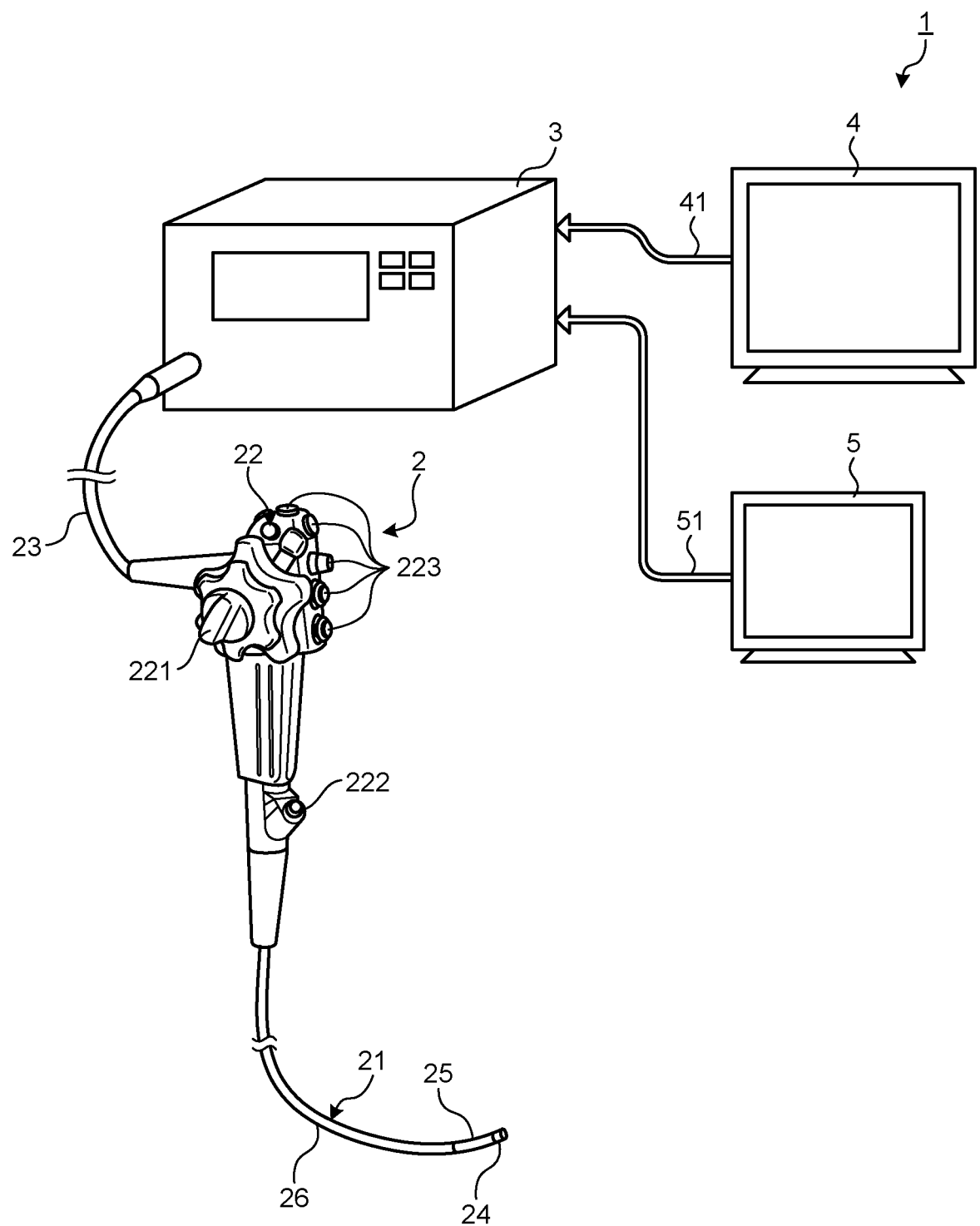
FIG. 1 is a diagram illustrating a schematic configuration of an endoscope system according to a first embodiment of the disclosure.
Figure 2:
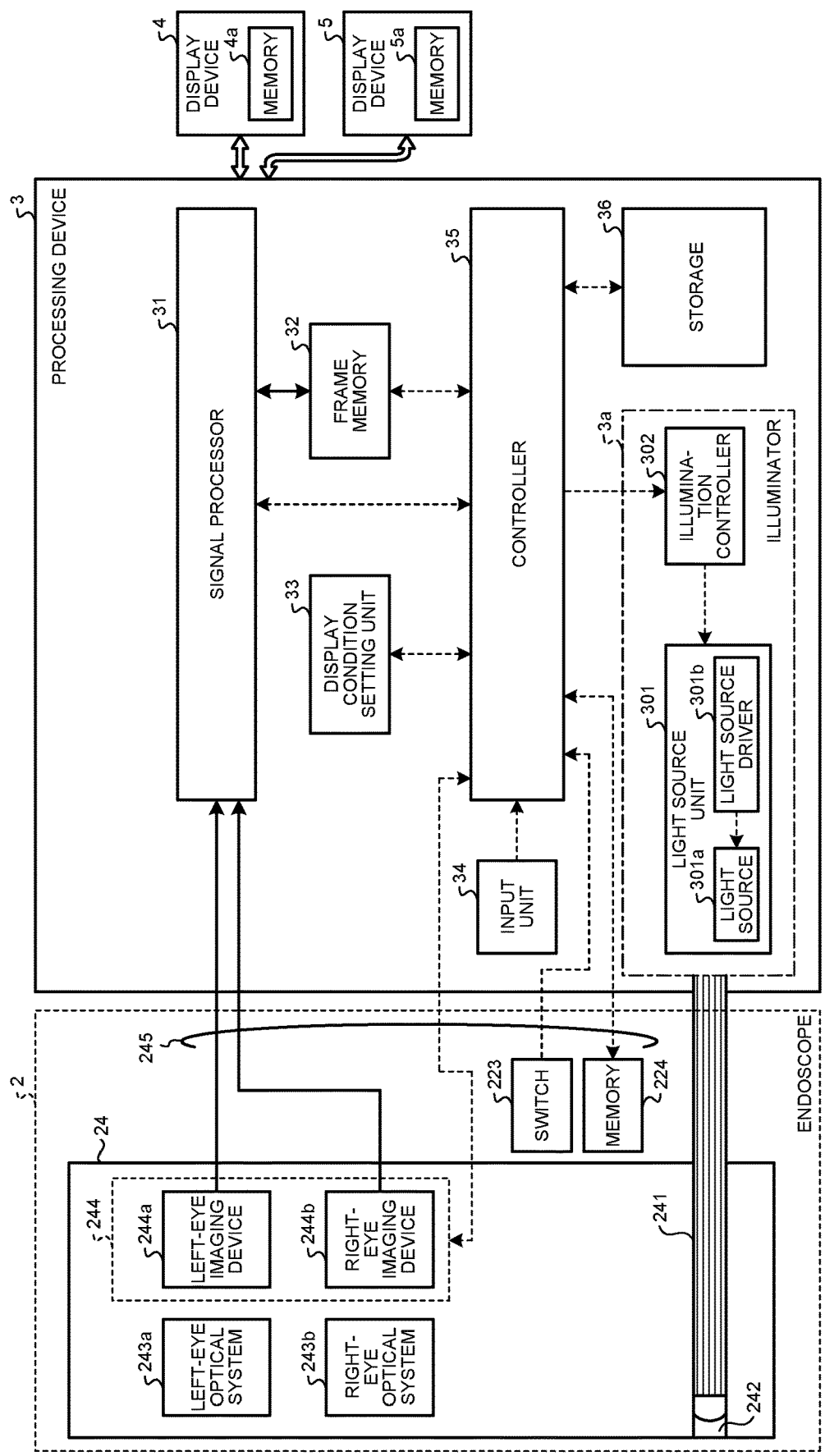
FIG. 2 is a block diagram illustrating a schematic configuration of the endoscope system according to the first embodiment of the disclosure.

FIG. 1 is a diagram illustrating a schematic configuration of an endoscope system according to a first embodiment of the disclosure. FIG. 2 is a block diagram illustrating a schematic configuration of the endoscope system according to the first embodiment of the disclosure.

An endoscope system 1 illustrated in FIGS. 1 and 2 includes an endoscope 2 whose distal end part is inserted into a subject to capture in-vivo images of the subject; a processing device 3 (endoscope processor) including an illuminator 3a that generates illumination light to be emitted from the distal end of the endoscope 2, that performs given signal processing on a signal of an image captured by the endoscope 2 (image data), and that performs overall control on operations over the endoscope system 1; and display devices 4 and 5 that display an in-vivo image that is generated by image processing performed by the processing device 3. Note that, in FIG. 2, the arrows in solid lines indicate transmission of electric signals on images and arrows in dotted lines indicate transmission of electric signals on control.

The endoscope 2 includes an insertion unit 21 that is flexible and elongated, an operation unit 22 that is connected to a proximal end side of the insertion unit 21 and receives inputs of various operation signals, and a universal cord 23 that extends in a direction different from a direction in which the insertion unit 21 extends from the operation unit 22 and that incorporates various cables that are connected to the processing device 3 (including the illuminator 3a).

The insertion unit 21 includes a distal end part 24 that incorporates an imager 244 in which pixels that receive light, perform photoelectric conversion, and thus generate signals are arrayed, a curve part 25 that is formed of multiple curve pieces, and a flexible tube 26 that is flexible and elongated and that is connected to the proximal end side of the curve part 25. The insertion unit 21 is inserted into a body cavity of the subject and captures images of a subject, such as living tissue to which external light does not reach, using the imager 244.

The distal end part 24 includes a light guide 241 that is configured using glass fibers and that forms a light guide path for light that is emitted by the illuminator 3a; an illumination lens 242 that is arranged at the distal end of the light guide 241; a left-eye optical system 243a and a right-eye optical system 243b for light convergence; and the imager 244 that is arranged in an imaging position of the left-eye optical system 243a and the right-eye optical system 243b, receives the light converged by the left-eye optical system 243a and the right-eye optical system 243b, converts the light into an electric signal by performing photoelectric conversion, and performs given image processing on the electric signal.

The left-eye optical system 243a is configured using at least one lens, is arranged before the imager 244, and forms an image of light from the subject. The left-eye optical system 243a may have an optical zoom function of varying the angle of view and a focus function of varying the focal point.

The right-eye optical system 243b is configured using at least one lens, is arranged before the imager 244, and forms an image of light from the subject. Parallax occurs between a subject image that is formed by the right-eye optical system 243b and a subject image that is formed by the left-eye optical system 243a. The right-eye optical system 243b may have the optical zoom function of varying the angle of view and the focus function of varying the focal point.

The imager 244 includes a left-eye imaging device 244a and a right-eye imaging device 244b.

According to a drive signal that is received from the processing device 3, the left-eye imaging device 244a performs photoelectric conversion on light from the left-eye optical system 243a and generates an electric signal of one frame forming one image (left-eye RAW data). Specifically, in the left-eye imaging device 244a, a plurality of pixels each including a photo diode that stores an electric charge corresponding to a volume of light, a capacitor that converts the charge that is transferred from the photodiode to a voltage level, etc., are arranged in a matrix and each of the pixels performs photoelectric conversion on light from the left-eye optical system 243a and generates an electric signal, and electric signals that are generated by pixels that are set freely as subjects from which signals are to be read among the pixels are read sequentially and are output as image data serving as left-eye RAW data. For example, a color filter is arranged on a light receiving surface of the left-eye imaging device 244a and each of the pixels receives light of any one of the bands of wavelength of color components of red (R), green (G), and blue (B).

According to a drive signal that is received from the processing device 3, the right-eye imaging device 244b performs photoelectric conversion on light from the right-eye optical system 243b and generates an electric signal of one frame forming one image (right-eye RAW data). Specifically, in the right-eye imaging device 244b, a plurality of pixels each including a photo diode that stores an electric charge corresponding to a volume of light, a capacitor that converts the charge that is transferred from the photodiode to a voltage level, etc., are arranged in a matrix and each of the pixels performs photoelectric conversion on light from the right-eye optical system 243b and generates an electric signal, and electric signals that are generated by pixels that are set freely as subjects from which signals are to be read among the pixels are read sequentially and are output as image data serving as right-eye RAW data. For example, a color filter is arranged on a light receiving surface of the right-eye imaging device 244b and each of the pixels receives light of any one of the bands of wavelength of color components of red (R), green (G), and blue (B).

The left-eye imaging device 244a and the right-eye imaging device 244b are implemented using, for example, a charge coupled device (CCD) image sensor or a complementary metal oxide semiconductor (CMOS) image sensor. Each of the left-eye imaging device 244a and the right-eye imaging device 244b may be configured using a single-board image sensor or, for example, may be formed of triple-board multiple image sensors.

A left-eye image obtained using the left-eye imaging device 244a and a right-eye image obtained using the right-eye imaging device 244b are images of different fields of view on a common subject and are images with parallax.

The imager 244 according to the first embodiment is described as one including two imaging devices corresponding to the left-eye optical system 243a and the right-eye optical system 243b, respectively, and each of the imaging devices generates an electric signal (image data) of one frame forming one image. In the first embodiment, sets of light that are formed by the left-eye optical system 243a and the right-eye optical system 243b are described as ones received by the two imaging devices corresponding to the left-eye optical system 243a and the right-eye optical system 243b. Alternatively, the sets of light may be received by the same imaging device in separated light reception areas.

The operation unit 22 includes a curve knob 221 that causes the curve unit 25 to curve in the up and down directions and the left and right direction; a treatment tool insertion port 222 into which a treatment tool, such as biopsy forceps, an electric scalpel, or an examination probe is inserted; and multiple switches 223 serving as an operation input unit that, in addition to the processing device 3, inputs operation instruction signals to an air supply unit and a water supply unit and for screen display control because of freeze processing, or the like. The treatment tool that is inserted from the treatment tool insertion port 222 goes out of an opening (not illustrated in the drawing) via a treatment tool channel (not illustrated in the drawing) of the distal end part 24. The switches 223 include a switch for inputting an instruction to set a measurement mode to be described below and a switch for inputting a freeze instruction to which instruction signals that are output by pressing are assigned, respectively.

The endoscope 2 further includes a memory 224 that records information on the endoscope 2. The memory 224 records identifying information representing the type and model number of the endoscope 2 and the types of the left-eye imaging device 244a and the right-eye imaging device 244b. The memory 224 may record various parameters for image processing on the data of images that are captured by the left-eye imaging device 244a and the right-eye imaging device 244b, such as a parameter for adjusting the white balance (WB) and a correction value on variation of the endoscope 2 on production.

The universal cord 23 incorporates at least the light guide 241 and an assembly cable 245 including a single signal line or a bundle of signal lines. The assembly cable 245 includes a signal line for transmitting image data, a signal line for transmitting a drive signal to drive the imager 244, and a signal line for transmitting and receiving information containing unique information on the endoscope 2 (the imager 244). In the first embodiment, supposing that electric signals are transmitted using the signal lines, description is given. Alternatively, optical signals may be transmitted or signals may be transmitted between the endoscope 2 and the processing device 3 by wireless communication.

When the endoscope 2 is mounted on the processing device 3, the information on the endoscope 2 described above is output to the processing device 3 by a process of communication with the processing device 3. Alternatively, a connection pin may be arranged in a connector according to rules corresponding to the information on the endoscope 2 and the processing device 3 may recognize connection of the endoscope 2 based on the state of connection between the connection pin on the side of the processing device 3 and the connection pin on the side of the endoscope 2 when the endoscope 2 is mounted.

A configuration of the processing device 3 will be described. The processing device 3 includes a signal processor 31, a frame memory 32, a display condition setting unit 33, an input unit 34, a controller 35, and a storage 36.

The signal processor 31 perform signal processing on the left-eye image data (analog) that is output from the left-eye imaging device 244a and the right-eye image data (analog) that is output from the right-eye imaging device 244b and generates display image data to be displayed on the display device 4 or the display device 5. The signal processor 31 corresponds to a signal processor. The signal processor 31 is configured using a dedicated processor, such as various processing circuits that implement specific functions, such as a general-purpose processor like a central processing unit (CPU), an application specific integrated circuit (ASIC), or a field programmable gate array (FPGA) that is a programmable logic device whose processing content is rewritable. Details of the signal processor 31 will be described below.

The signal processor 31 generates a parallax image obtained by causing parallax by shifting the left-eye image and the right-eye image with respect to the left-eye image data and the right-eye image data and performs signal processing to generate a signal in a form displayable on the display device 4, thereby generating display image data. Specifically, the signal processor 31 relatively shifts the right-eye image and the left-eye image based on a monitor shift value that is set by the display condition setting unit 33, thereby generating display image data.

Figures 3, 4:
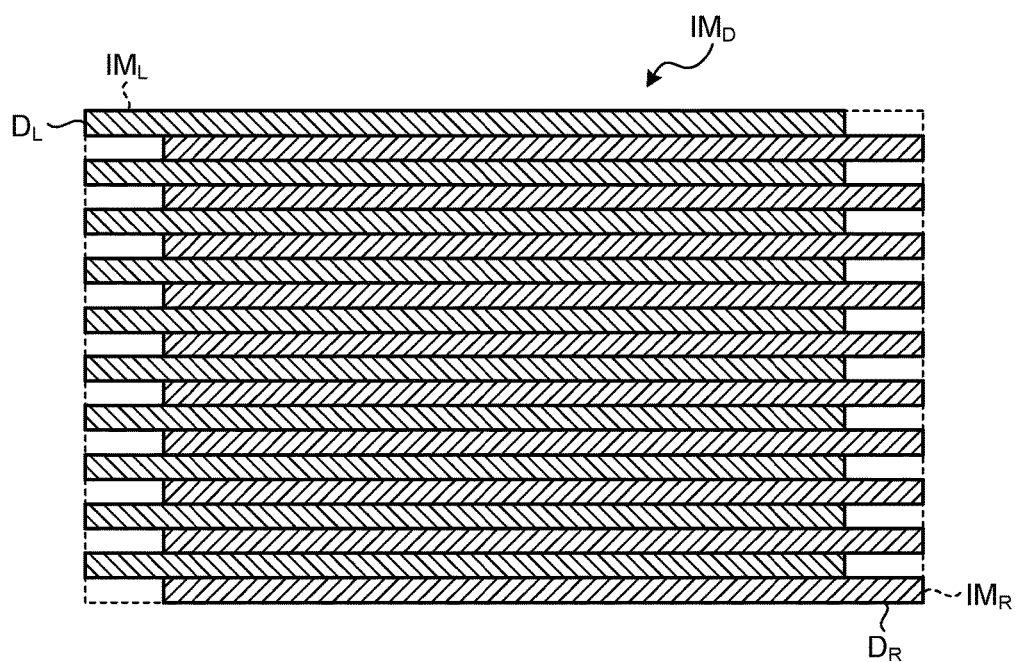
FIG. 3 is a diagram to explain an example of a parallax image that is generated by the endoscope system according to the first embodiment of the disclosure.
FIG. 4 is a diagram illustrating an example of a monitor shift value determination table that is stored in a storage of the endoscope system according to the first embodiment of the disclosure.

With reference to FIG. 3, the parallax image that is generated by the signal processor 31 will be described. FIG. 3 is a diagram to explain the parallax image that is generated by the endoscope system according to the first embodiment of the disclosure. The signal processor 31 generates a parallax image $IM_D$ by alternately shifting and arranging line images $D_L$ of horizontal lines in a left-eye image IME and line images $D_R$ of horizontal lines in a right-eye image $IM_R$ according to a monitor shift value that is set. Specifically, the signal processor 31 alternately shifting and arranging the line images $D_L$ of odd-number horizontal lines of the left-eye image IME and the line images $D_R$ of even-number horizontal lines of the right-eye image $IM_R$ according to an amount of shift that is set. The parallax image $IM_D$ is also referred to as a line-by-line image. The horizontal lines here correspond to lines formed by pixels that are arranged along one of the array directions in the imaging device in which the pixels are arranged in a matrix. An observer is able to three-dimensionally observe the image by viewing the above-described parallax image using an assisting tool, such as three-dimensional observation glasses.

The frame memory 32 stores a set number of frames of display image data that is generated by the signal processor 31. In the first embodiment, the frame memory 32 stores display image data of few frames. When new image data is input, the frame memory 32 rewrites the oldest image data among the image data that is stored currently with the new image data, thereby storing the image data while sequentially updating the image data of the few frames in the ascending order of times at which image data is generated. The frame memory 32 is configured using a random access memory (RAM), such as a video RAM (VRAM).

Based on information of the model of the display device (the display device 4 or the display device 5) that is connected to the processing device 3, the display condition setting unit 33 sets conditions on displaying images to be displayed on the connected display device. Specifically, in the first embodiment, the display condition setting unit 33 sets a monitor shift value according to the type of the endoscope 2 and the model of the display device that is connected to the processing device 3. The monitor shift value corresponds to the amount of shift between the left-eye image and the right-eye image on the display screen. The display condition setting unit 33 refers to the storage 36 and sets a monitor shift value corresponding to the monitor size of the connected display device. The display condition setting unit 33 is configured using a general-purpose processor, such as a CPU, or dedicated processors, such as various operation circuits that execute given functions of an ASIC, a FPGA, etc.

The input unit 34 is implemented using a keyboard, a mouse, a switch, and a touch panel and receives inputs of various signals, such as an operation instruction signal of an instruction for an operation of the endoscope system 1. The input unit 34 may contain a switch that is provided in the operation unit 22 and a portable terminal device, such as an external tablet computer.

The controller 35 performs control to drive components including the imager 244 and the illuminator 3a and control to input and output information to and from each component. The controller 35 refers to control information data (for example, read timing) for imaging control that is stored in the storage 36 and transmits the control information data to the imager 244 as a drive signal via a given signal line contained in the assembly cable 245.

The controller 35 acquires information on a monitor size from the display device that is connected to the processing device 3. The information on the monitor size that is acquired by the controller 35 is output to the display condition setting unit 33. The controller 35 functions as an acquisition circuit that acquires the monitor size information. The controller 35 is configured using a general-purpose processor, such as a CPU, or dedicated processors, such as various operation circuits that execute given functions of an ASIC, a FPGA, etc.

The storage 36 stores various programs for causing the endoscope system 1 to operate and data containing various parameters necessary for operations of the endoscope system 1. The storage 36 further stores identifying information of the processing device 3 and a monitor shift value determination table for determining a monitor shift value from the type of the endoscope 2 and the monitor size. The identifying information contains unique information (ID), a model year, and specification information on the processing device 3.

FIG. 4 is a diagram illustrating an example of the monitor shift value determination table that is stored in the storage of the endoscope system according to the first embodiment of the disclosure. In the monitor shift value determination table, models of the endoscope 2 and monitor shift values corresponding to monitor sizes of the display device are preset. In the monitor shift value determination table, even for the same monitor size, monitor shift values are set independently according to the models of the endoscope 2 (for example, properties of imaging devices of imagers of various endoscopes). The monitor shift values that are set in the monitor shift value determination table are values that do not cause divergence when the observe views a display image that is displayed on the display device.

Note that the monitor shift value determination table may be provided for each observation method (such as observation using white light or NBI observation) or each region to be observed.

The storage 36 stores various programs containing an image processing program for executing an image processing method employed by the processing device 3. The various programs can be recorded in a computer-readable recording medium, such as a hard disk, a flash memory, a CD-ROM, a DVD-ROM, or a flexible disk, and distributed widely. The aforementioned various programs can be also acquired by being downloaded via a communication network. The communication network herein is implemented using, for example, an existing public network, a local area network (LAN), or a wide area network (WAN) and whether the communication network is wired or wireless does not matter.

The storage 36 having the above-described configuration is implemented using a read only memory (ROM) in which the various programs, etc., are installed previously, a RAM or a hard disk that stores operation parameter and data on each processing, etc.

A configuration of the illuminator 3a will be described. The illuminator 3a includes a light source unit 301 and an illumination controller 302. The light source unit 301 emits illumination light to a subject (the subject) under the control of the illumination controller 302. The light source unit 301 includes a light source 301a and a light source driver 301b.

The light source 301a is configured using a light source that emits white light, at least one lens, etc., and, when the LED light source is drive, accordingly emits light (illumination light). The illumination light that is generated by the light source 301a is emitted from the distal end of the distal end part 24 toward the subject via the light guide 241. In the first embodiment, supposing that white light is emitted, description is given. Alternatively, for NBI observation, the light source 301a may emit, as the illumination light, narrowband light formed of narrowband light of blue (for example, 390 nm to 445 nm) and narrowband light of green (for example, 530 nm to 550 nm) or the white light and the narrow-band light may be switched in between. The light source 301a is implemented using any one of an LED light source, a laser light source, a xenon lump, and a halogen lamp.

Under the control of the illumination controller 302, the light source driver 301b supplies power to the light source 301a to cause the light source 301a to emit illumination light.

Based on a control signal (modulated light signal) from the controller 35, the illumination controller 302 controls the amount of power supplied to the light source 301a and controls the timing at which the light source 301a is driven.

The display device 4 is connected detachably to the processing device 3 and displays a display image corresponding to display image data that is received from the processing device 3 (the frame memory 32), etc., via a video cable 41. The display device 4 is configured using a liquid crystal or organic electro luminescence (EL) monitor, or the like.

The display device 5 is connected detachably to the processing device 3 and displays a display image corresponding to display image data that is received from the processing device 3 (the frame memory 32), etc., via a video cable 51. The display device 5 has a monitor size smaller than that of the display device 4. The display device 5 is configured using a liquid crystal or organic electro luminescence (EL) monitor, or the like.

In the first embodiment, the display devices 4 and 5 respectively include memories 4a and 5a each of which stores model information, such as information on the monitor size of the display device. When being connected to the processing device 3, the display devices 4 and 5 output the model information according to requests from the controller 35.

The video cables 41 and 51 (including terminals) contain video data channels to communicate display data, such as display image data, and display data channels (DDC) to communicate extended display identification data (EDID), such as a recommended resolution and a refresh note.

Figure 5:
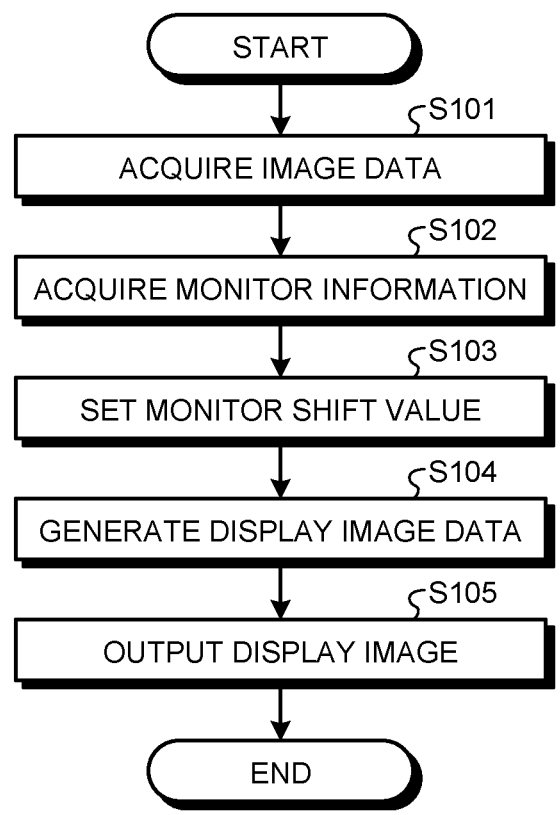
FIG. 5 is a flowchart representing a process that is performed by the endoscope system according to the first embodiment of the disclosure.

Image processing performed by the endoscope system 1 will be described. FIG. 5 is a flowchart representing a process that is performed by the endoscope system according to the first embodiment of the disclosure. Supposing that each unit operates under the control of the controller 35, description is given below.

First of all, the processing device 3 acquires image data from the endoscope 2 (step S101). The controller 35 acquires information of the monitor size (monitor information) from the display device (the display device 4 or the display device 5) that is connected to the processing device 3 (step S102).

At step S103 following step S102, the display condition setting unit 33 refers to the monitor shift value determination table that is stored in the storage 36 and sets a monitor shift value corresponding to the monitor size of the connected display device.

As for steps S101 to S103 described above, steps S102 and S103 may be executed prior to step S101. Acquiring monitor information and setting a monitor shift value may be executed when the display device is connected to the processing device 3 regardless whether the endoscope is driven.

At step S104, the signal processor 31 relatively shifts a right-eye image and a left-eye image based on the monitor shift value that is set by the display condition setting unit 33 and performs signal processing to generate a signal in a form displayable on the display device 4, thereby generating display image data. The signal processor 31 stores the generated display image data in the frame memory 32.

At step S105 following step S104, the controller 35 outputs a display image to the connected display device. Specifically, the controller 35 causes the display device to display a parallax image corresponding to the display image data. The controller 35 sequentially outputs the display image data that is stored in the frame memory 32 to the display device and causes the display device to display the image. The parallax image that is controlled at an amount of shift that does not cause divergence to an observer is displayed on the display device.

The above-described first embodiment employs the configuration in which the monitor shift value corresponding to the amount of shift between the left-eye image and the right-eye image is set at a value that does not cause divergence according to the monitor size of the display device that is connected to the processing device 3. According to the first embodiment, when a parallax image is displayed, it is possible to inhibit divergence to the eyes of the observer.

In the first embodiment described above, the controller 35 may choose the best frame with small fluctuations when outputting the display image data to the display device. For example, the display controller 35 calculates an amount of fluctuation of the display image data that is stored in the frame memory 32 and chooses, as image data to be displayed on the display device, the display image data with the smallest fluctuation.

When the monitor size increases, even with a small shift value, the amount of shift between the right-eye image and the left-eye image is shown greater and there is a risk that divergence be caused. Modifications for inhibiting divergence caused by a large monitor size will be described.

Modification 1 of First Embodiment

The above-described first embodiment employs the configuration in which the monitor shift value corresponding to the amount of shift between the left-eye image and the right-eye image is changed, and the display condition setting unit 33 may control the size of the parallax image based on the acquired monitor information. For example, a configuration in which, when the monitor size is large, parallax on the observer is reduced by, for example, reducing the size of the parallax image is employed.

Figure 6:
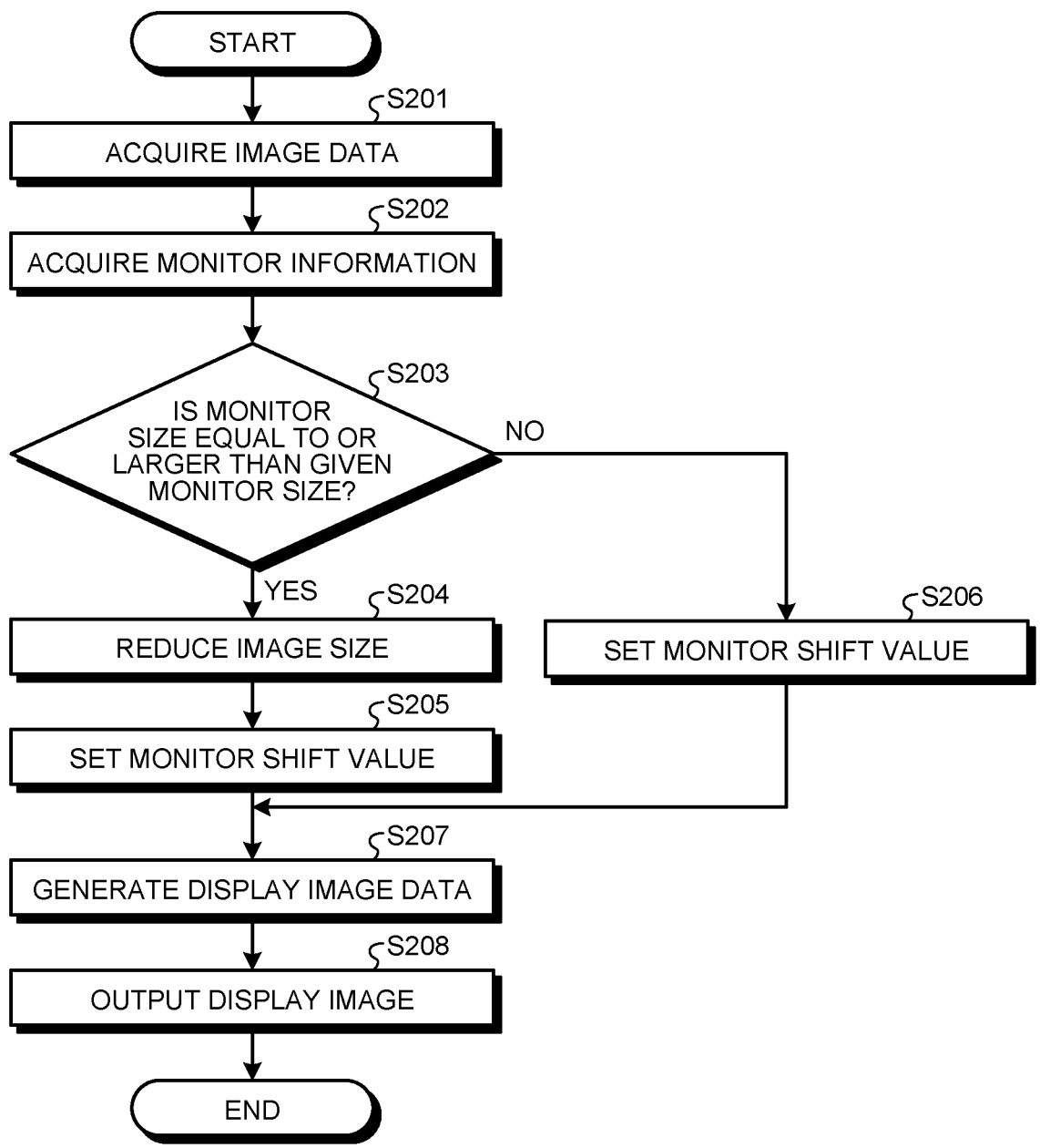
FIG. 6 is a flowchart representing a process that is performed by an endoscope system according to Modification 1 of the first embodiment of the disclosure.

FIG. 6 is a flowchart representing a process that is performed by an endoscope system according to Modification 1 of the first embodiment of the disclosure. Supposing that each unit operates under the control of the controller 35, description is given below.

First of all, the processing device 3 acquires image data from the endoscope 2 (step S201). The controller 35 acquires information on the monitor size (monitor information) from a display device that is connected to the processing device 3 (step S202).

At step S203 following step S202, the display condition setting unit 33 compares the monitor size of the connected display device and a monitor size that is preset (a given monitor size). When the monitor size of the connected display device is equal to or larger than the given monitor size (YES at step S203), the display condition setting unit 33 moves to step S204.

At step S204, the display condition setting unit 33 reduces the size of display of a parallax image on the display device (image size). After setting the image size, the display condition setting unit 33 moves to step S205.

At step S205, the display condition setting unit 33 sets a monitor shift value corresponding to the monitor size of the connected display device. As long as no divergence is caused in the parallax image after the size is changed, the monitor shift value may be a value that causes divergence in a parallax image when the parallax image is generated before the size is changed. After setting the monitor shift value, the display condition setting unit 33 moves to step S207.

On the other hand, when the monitor size of the connected display device is smaller than the given monitor size (NO at step S203), the display condition setting unit 33 moves to step S206.

At step S206, as at step S103 described above, the display condition setting unit 33 refers to the monitor shift value determination table and sets a monitor shift value corresponding to the monitor size of the connected display device. After setting the monitor shift vale, the display condition setting unit 33 moves to step S207.

At step S207, the signal processor 31 relatively shifts a right-eye image and a left-eye image based on the image size and the monitor shift value that are set by the display condition setting unit 33 or the monitor shift value and performs single processing to generate a signal in a form displayable on the display device 4, thereby generating display image data. The signal processor 31 stores the generated display image data in the frame memory 32.

At step S208 following step S207, the controller 35 causes the connected display device to display a parallax image corresponding to the display image data. The controller 35 sequentially outputs the display image data that is stored in the frame memory 32 to the display device and causes the display device to display the image. At that time, the parallax image that is controlled at an image size that does not cause divergence to the user or the parallax image that is controlled at an amount of shift that does not cause divergence to the observer is displayed on the display device is displayed.

Modification 1 employs the configuration in which the image size of the parallax image is reduced according to the monitor size or the monitor shift value corresponding to the amount of shift between the left-eye image and the right-eye image is set at a value that does not cause divergence according to the monitor size of the display device that is connected to the processing device 3.

According to Modification 1, it is possible to inhibit divergence to the eyes of the observer.

Modification 2 of First Embodiment

The above-described first embodiment employs the configuration in which the monitor shift value corresponding to the amount of shift between the left-eye image and the right-eye image is changed and, a setting for displaying an image two-dimensionally when the monitor size is equal to or larger than a pre-set monitor size is made. Any one of the right-eye image data and the right-eye image data is chosen as the display image data.

Figure 7:
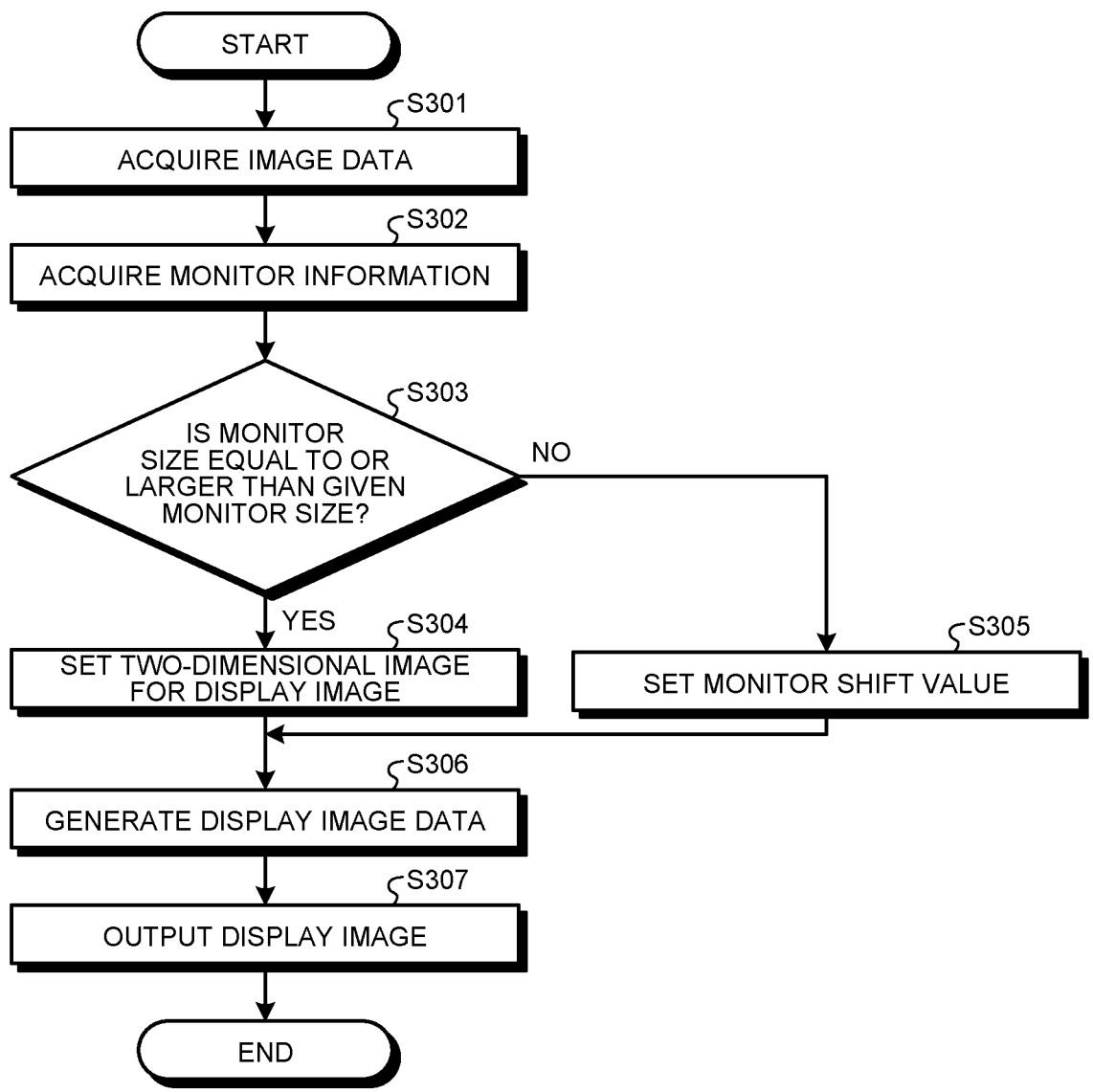
FIG. 7 is a flowchart representing a process that is performed by an endoscope system according to Modification 2 of the first embodiment of the disclosure.

FIG. 7 is a flowchart representing a process performed by an endoscope system according to Modification 2 of the first embodiment of the disclosure. Supposing that each unit operates under the control of the controller 35, description is given below.

First of all, the processing device 3 acquires image data from the endoscope 2 (step S301). The controller 35 acquires information on the monitor size (monitor information) from a display device that is connected to the processing device 3 (step S302).

At step S303 following step S302, the display condition setting unit 33 compares the monitor size of the connected display device and a monitor size that is preset (given monitor size). When the monitor size is equal to or larger than the given monitor size (YES at step S303), the display condition setting unit 33 moves to step S304.

At step S304, the display condition setting unit 33 sets a two-dimensional image for an image to be displayed on the display device. The display condition setting unit 33 specifies any one of left-eye image data and right-eye image data as image data to be used to generate a two-dimensional image. The image data (the left-eye image data or the right-eye image data) to be specified by the display condition setting unit 33 is preset. After setting the display image, the display condition setting unit 33 moves to step S306.

On the other hand, when the monitor size is smaller than the given monitor size (NO at step S303), the display condition setting unit 33 moves to step S305.

At step S305, as at step S103 described above, the display condition setting unit 33 refers to the monitor shift value determination table and sets a monitor shift value corresponding to the monitor size of the connected display device. After setting the monitor shift value, the display condition setting unit 33 moves to step S306.

At step S306, the signal processor 31 generates display image data based on one of the sets of image data that is specified by the display condition setting unit 33 or generates display image data by relatively shifting a right-eye image and a left-eye image based on the monitor shift value that is set by the display condition setting unit 33 and performing signal processing to generate a signal in a form displayable on the display device 4. The signal processor 31 stores the generated display image data in the frame memory 32.

At step S307 following step S306, the controller 35 causes the connected display device to display a parallax image corresponding to the display image data. The controller 35 sequentially outputs the display image data that is stored in the frame memory 32 to the display device and causes the display device to display the image. A parallax image that is controlled at an image size that does not cause divergence to the observer or a parallax image that is controlled at an amount of shift that does not causes divergence to the observer is displayed.

Modification 2 described above employs the configuration in which a two dimensional image is set for the display image according to the monitor size or the monitor shift value corresponding to the amount of shift between the left-eye image and the right-eye image is set at a value that does not cause divergence according to the monitor size of the display device that is connected to the processing device 3. According to Modification 2, it is possible to inhibit divergence to the eyes of the observer when the parallax image is displayed.

Note that a configuration in which the observer is able to choose one of the processes of the first embodiment, Modification 1, and Modification 2 by operating the input unit 34 may be employed.

Second Embodiment

Figure 8:
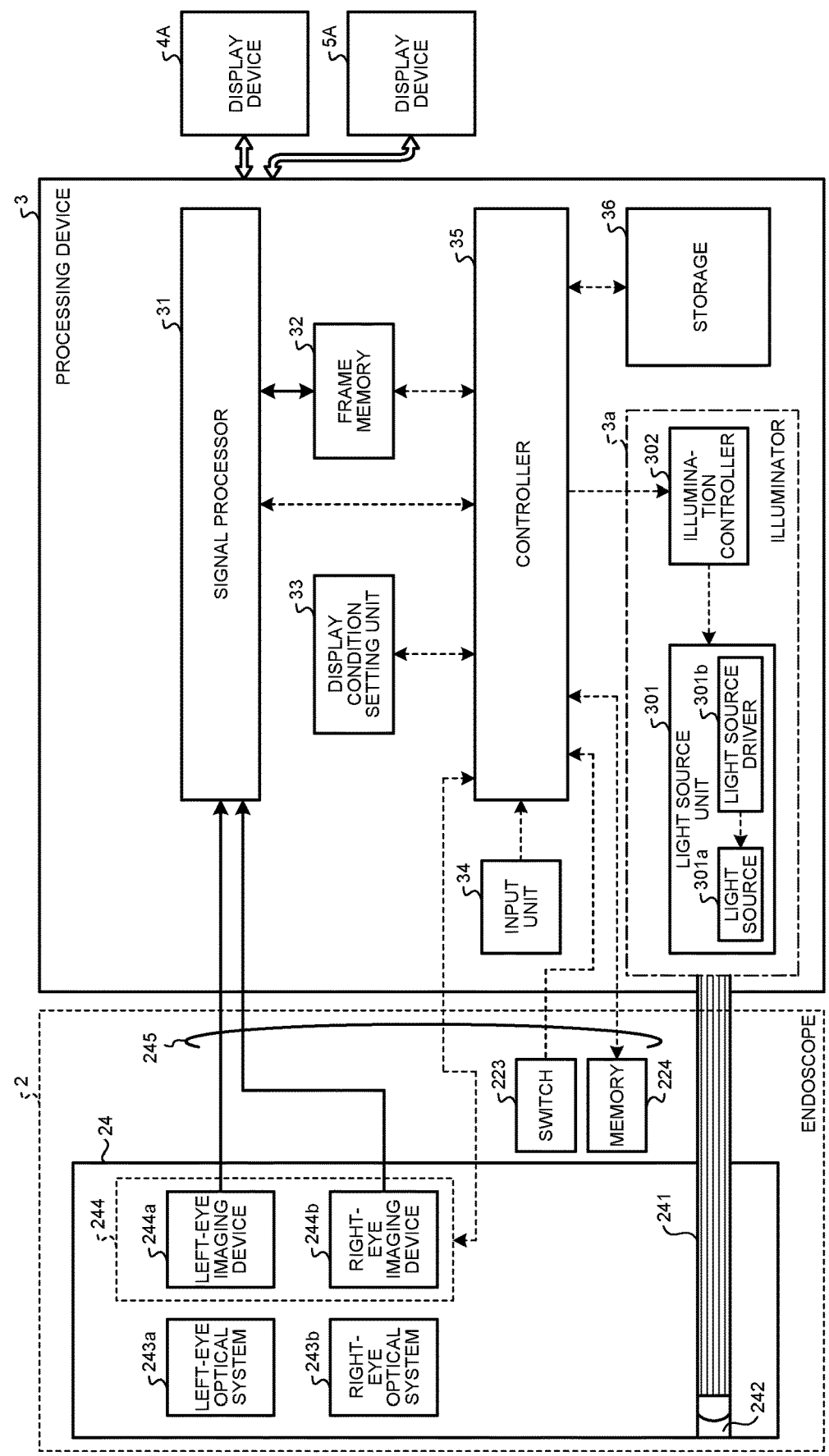
FIG. 8 is a block diagram illustrating a schematic configuration of an endoscope system according to a second embodiment of the disclosure.

A second embodiment of the disclosure will be described with reference to FIG. 8. FIG. 8 is a block diagram illustrating a schematic configuration of an endoscope system according to the second embodiment of the disclosure.

An endoscope system 1A according to the second embodiment includes the endoscope 2 and the processing device 3 (endoscope processor) that are described above and display devices 4A and 5A that display in-vivo images that are generated by image processing performed by the processing device 3. The endoscope system 1A according to the second embodiment has the same configuration as that of the first embodiment excluding the aspect that the display devices 4 and 5 of the above-described endoscope system 1 are replaced with the display devices 4A and 5A. The processes performed by the display devices 4A and 5A with configurations different from those of the first embodiment and the processing device 3 will be described below.

The display devices 4A and 5A are detachably connected to the processing device 3 and display a display image corresponding to display image data that is received from the processing device 3 (the frame memory 32) via the video cable. The display devices 4A and 5A are configured using a liquid crystal or electro luminescence (EL) monitor, or the like. The display devices 4A and 5A according to the second embodiment have configurations without the memories 4a and 5a described above and other aspects are the same as those of the above-described display devices 4 and 5.

The processing device 3 according to the second embodiment does not store the above-described monitor shift value setting table. For this reason, the display condition setting unit 33 sets, for a monitor shift value, a value that is input by an observer by operating the input unit 34. The observer operates the input unit 34 and inputs a signal that specifies a monitor shift value according to the monitor size of the display device on which an image is displayed. As for the model of the endoscope 2 and determining a monitor shift value corresponding to the monitor size of the display device, as in the above-described first embodiment, a setting is made as appropriate according to determination by the observer or how a parallax image is shown.

The above-described second embodiment employs the configuration in which a monitor shift value corresponding to an amount of shift between a left-eye image and a right-eye image is set at a value that does not cause divergence to the observer according to the monitor size of the display device that is connected to the processing device 3. According to the second embodiment, it is possible to inhibit divergence to the eyes of the observer when the parallax image is displayed.

Third Embodiment

A third embodiment of the disclosure will be described. A configuration of the endoscope system according to the third embodiment is the same as that of the first embodiment. A process different from that of the first embodiment will be described below. In the third embodiment, the display device makes a multi-display of a parallax image.

Figure 9:
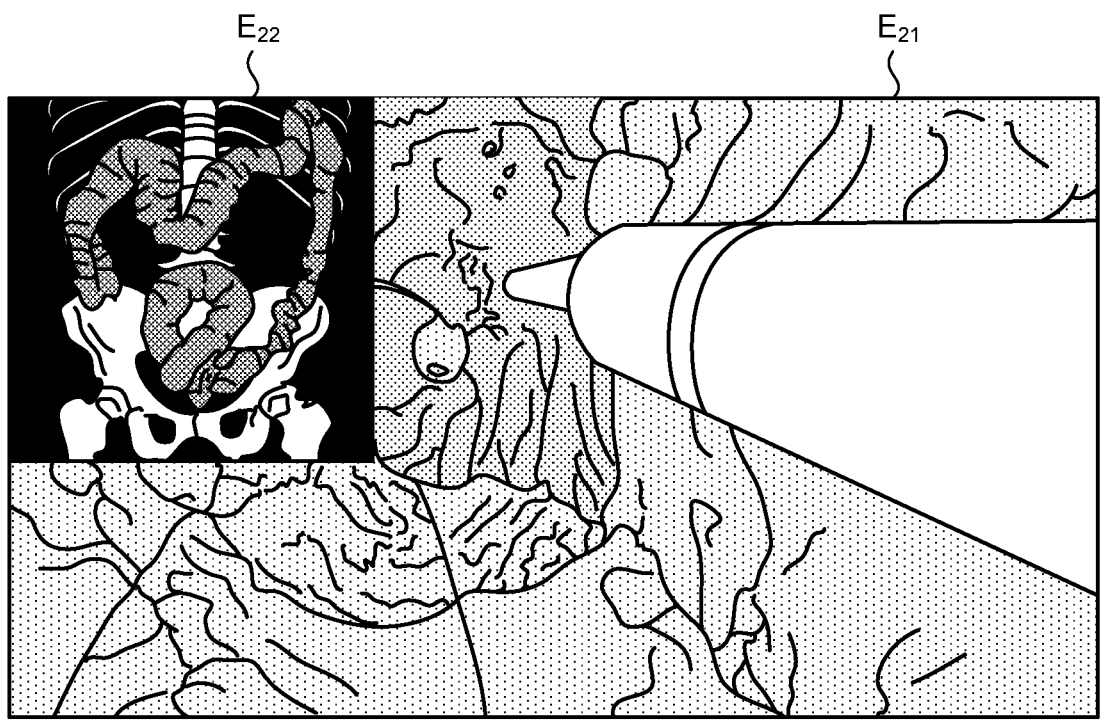
FIG. 9 is a diagram to explain an example of an image that is displayed by a display device of an endoscope system according to a third embodiment of the disclosure.

FIG. 9 is a diagram to explain an example of an image that is displayed on a display device of the endoscope system according to the third embodiment of the disclosure. The display device displays two parallax images illustrated in FIG. 9. Specifically, a first display area $E_{21}$ in which a parallax image that is captured by the endoscope 2 is displayed and a second display area $E_{22}$ in which a parallax image representing an internal structure of a subject into which the endoscope 2 is introduced (volume image) is displayed are set. The display condition setting unit 33 sets monitor shift values for the respective display areas. Supposing that the storage 36 stores monitor shift value setting tables on the respective display areas and image data on an internal structure of the subject (left-eye image data and right-eye image data), description is given below.

Figure 10:
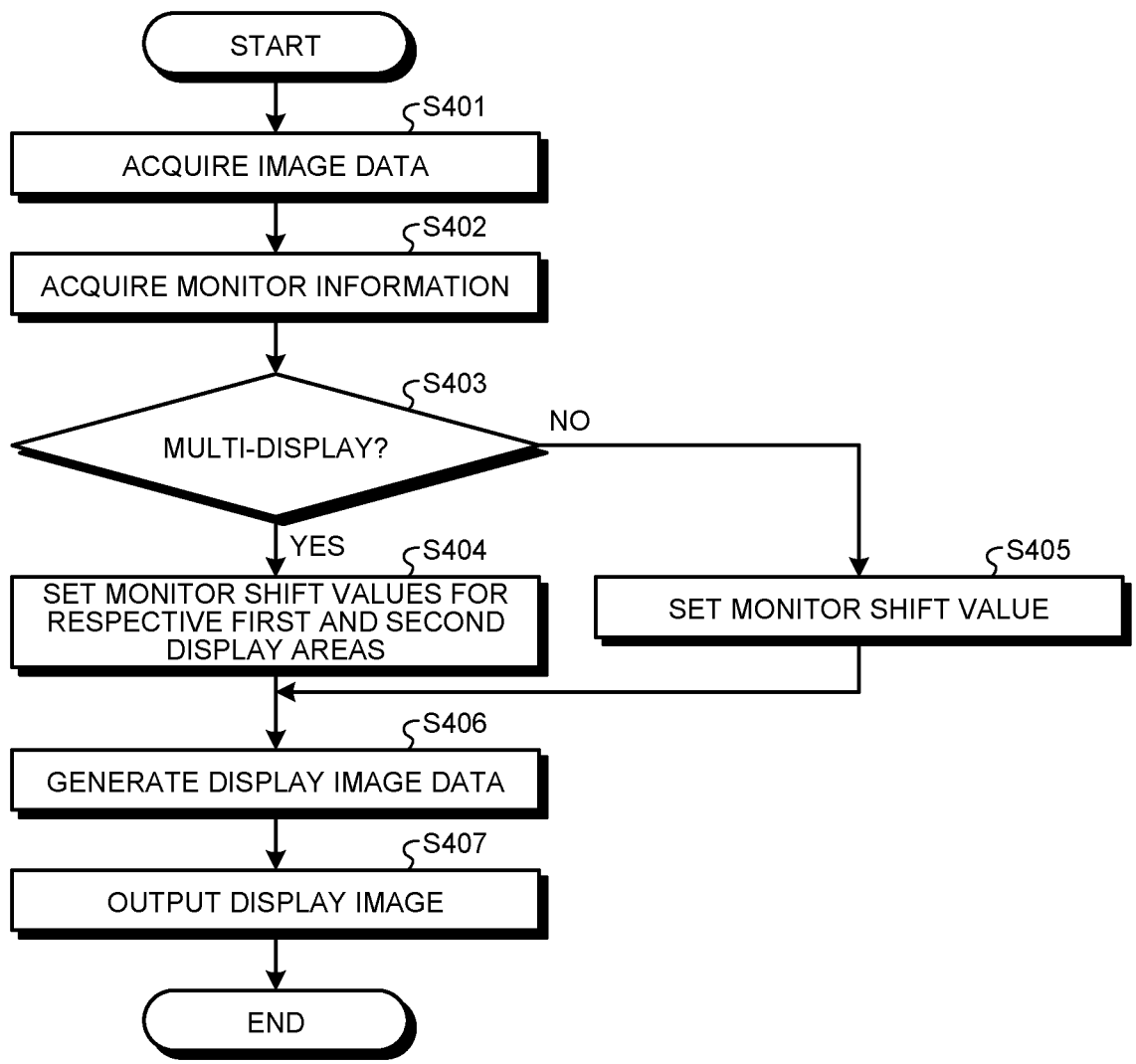
FIG. 10 is a flowchart representing a process that is performed by the endoscope system according to a third embodiment of the disclosure.

Image processing performed by the endoscope system 1 will be described. FIG. 10 is a flowchart representing a process performed by the endoscope system according to the third embodiment of the disclosure. Supposing that that each unit operates under the control of the controller 35, description is given below.

First of all, the processing device 3 acquires image data from the endoscope 2 (step S401). The controller 35 acquires information on the monitor size (monitor information) from a connected display device (the display device 4 or the display device 5) (step S402).

At step S403 following step S402, the controller 35 determines whether to make a multi-display on the display device from the monitor information. When it is determined to make a multi-display (YES at step S403), the controller 35 moves to step S404.

At step S404, the display condition setting unit 33 refers to the monitor shift value determination tables that are stored in the storage 36 and sets monitor shift values for respective display areas (for example, the first display area $E_{21}$ and the second display area $E_{22}$). After setting the monitor shift values, the controller 35 moves to step S406.

On the other hand, at step S403, when it is determined not to make a multi-display (NO at step S403), the controller 35 moves to step S405.

At step S405, as in the first embodiment, the display condition setting unit 33 refers to the monitor shift value setting table that is stored in the storage 36 and sets a monitor shift value corresponding to the monitor size of the connected display device. After setting the monitor shift value, the controller 35 moves to step S406.

At step S406, the signal processor 31 relatively shifts a right-eye image and a left-eye image based on the monitor shift value that is set by the display condition setting unit 33 and performs image processing to generate a signal in a form displayable on the display device 4, thereby generating display image data. The signal processor 31 stores the generated display image data in the frame memory 32.

At step S407 following step S406, the controller 35 causes the connected display device to display a parallax image corresponding to the display image data. The controller 35 sequentially outputs the display image data that is stored in the frame memory 32 to the display device and causes the display device to display the image.

The above-describe third embodiment employs the configuration in which, even when a multi-display is made on the display device, the monitor shift values for the respective display areas are set at values that does not cause divergence according to the display size. According to the third embodiment, even when a multi-display of the parallax image is made, it is possible to inhibit divergence to the eyes of the observer.

In the third embodiment of the disclosure described above, supposing that the internal structure of the subject (volume image) is displayed in the second display area $E_{22}$, description is given, and a virtual endoscope image that is generated from the volume image may be displayed or positional information on the endoscope 2 corresponding to the volume image, stereoscopic information (such as the distance between the optical axes of the respective optical systems and the imaging magnification), and information of the display size may be displayed.

Fourth Embodiment

Figure 11:
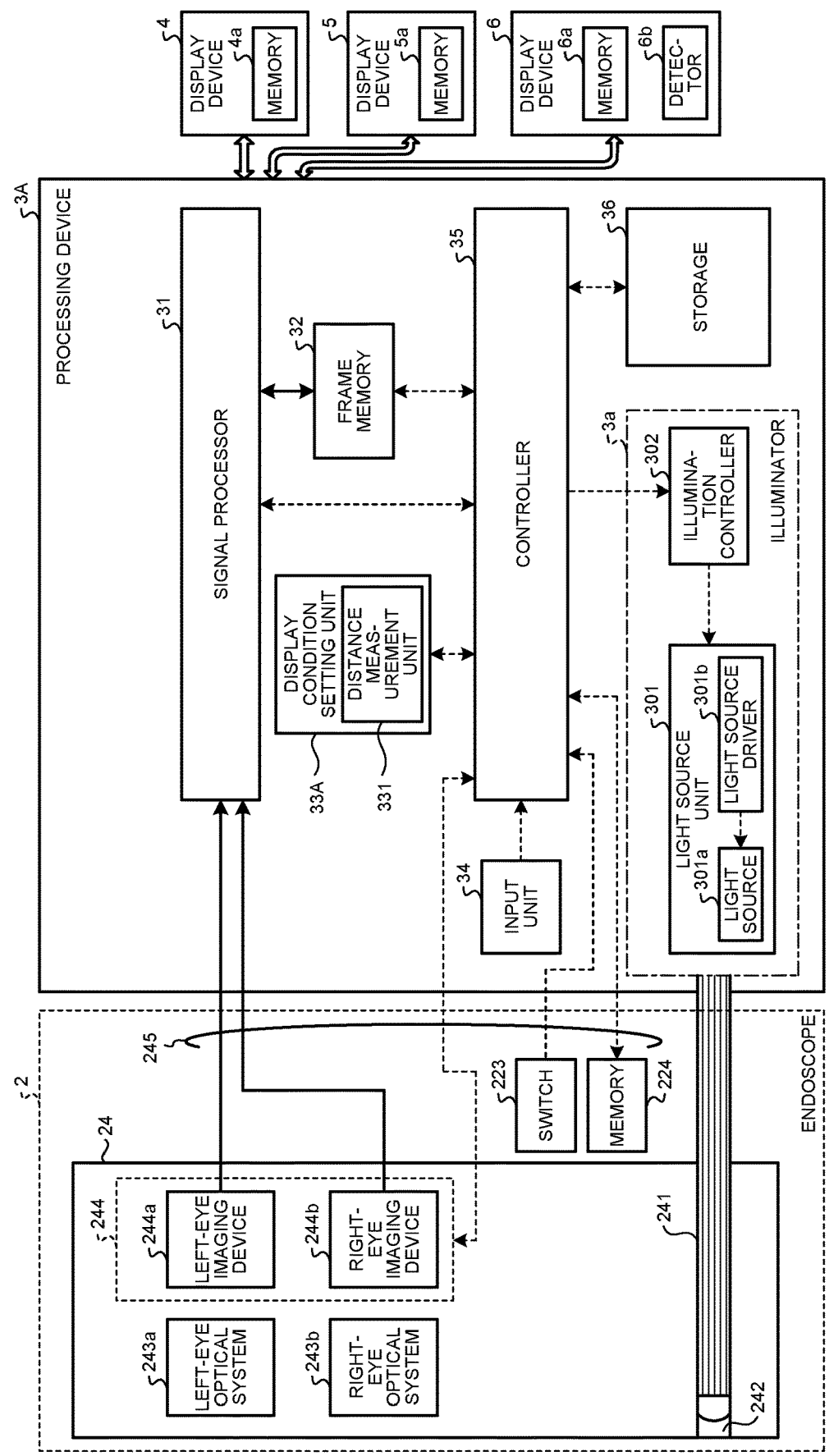
FIG. 11 is a block diagram illustrating a schematic configuration of an endoscope system according to a fourth embodiment of the disclosure.

A fourth embodiment of the disclosure will be described with reference to FIGS. 11 to 14. FIG. 11 is a block diagram illustrating a schematic configuration of an endoscope system according to the fourth embodiment of the disclosure.

An endoscope system 1B according to the forth embodiment includes the above-described endoscope 2, a processing device 3A (endoscope processor), and the display devices 4 and 5 and a display device 6 that display an in-vivo image that is generated by image processing performed by the processing device 3A. The endoscope system 1B according to the fourth embodiment has the same configuration as that of the above-described endoscope system 1 except for the aspect that the processing device 3 is replaced with the processing device 3A and the display device 6 is further connectable. Processes performed by the processing device 3A having a configuration different from that of the first embodiment and the display device 6 will be described below.

The processing device 3A includes the signal processor 31, the frame memory 32, a display condition setting unit 33A, the input unit 34, the controller 35, and the storage 36. The display condition setting unit 33A having a configuration different from that of the first embodiment will be described below.

The display condition setting unit 33A sets a monitor shift value according to the type of the endoscope 2 and the model of a display device that is connected to the processing device 3 (any one of the display devices 4, 5 and 6 in the fourth embodiment). The monitor shift value corresponds to the amount of shift between a left-eye image and a right-eye image on a display screen. The display condition setting unit 33 refers to the storage 36 and sets a monitor shift value corresponding to the monitor size of the connected display device.

The display condition setting unit 33A includes a distance measurement unit 331. Based on data (distance measurement image data to be described below) that is acquired by a stereo camera installed in the display device 6, the distance measurement unit 331 calculates a distance using the principle of triangulation. The distance measurement unit 331 is configured using a general-purpose processor, such as a CPU, or dedicated processors, such as various operation circuits that execute given functions of an ASIC, a FPGA, etc.

The display condition setting unit 33 calculates an appearance monitor size from the distance that is calculated by the distance measurement unit 331 and the monitor information (monitor size). The "appearance monitor size" herein refers to a possible image display size on the display device and is an image display size viewed from an observer on which the distance measurement is performed. The display condition setting unit 33 sets a monitor shift value from the appearance monitor size and the type of the endoscope 2. The storage 36 stores a monitor shift value determination table that is determined from the appearance monitor size and the type of the endoscope 2.

The display device 6 is detachably connected to the processing device 3A and displays a display image corresponding to display image data that is received from the processing device 3A (the frame memory 32), or the like, via the video cable. The display device 6 is configured using a liquid crystal or electro luminescence (EL) monitor, or the like.

The display device 6 includes a memory 6a that stores model information, such as the monitor size of the display device 6, and a detector 6b that detects information for measuring the distance between the display device 6 and the observer. When being connected to the processing device 3A, the display device 6 outputs the model information or the detection information according to a request from the controller 35.

Figure 12:
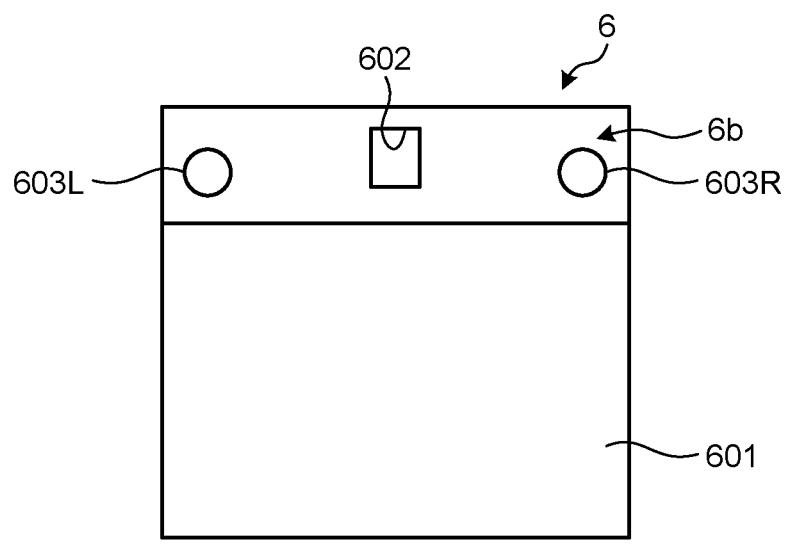
FIG. 12 is a diagram illustrating a schematic configuration of a display device of the endoscope system according to the fourth embodiment of the disclosure.

FIG. 12 is a diagram illustrating a schematic configuration of the display device of the endoscope system according to the fourth embodiment of the disclosure. The display device 6 includes a display area 601, an infrared light emitter 602 that emits infrared light, and two imagers (a first imager 603L and a second imager 603R) that capture infrared images that are generated from the infrared light that is reflected by an object. The infrared light emitter 602, the first imager 603L and the second imager 603R form the above-described detector 6b.

Figure 13:
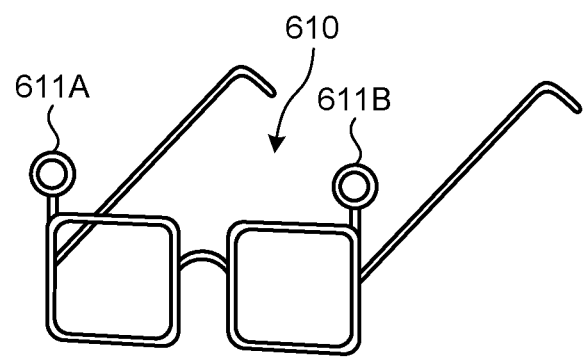
FIG. 13 is a diagram illustrating an example of a device for measuring a distance between the display device and a user in the endoscope system according to the fourth embodiment of the disclosure.

FIG. 13 is a diagram illustrating an example of a device for measuring the distance between the display device and the user in the endoscope system according to the fourth embodiment of the disclosure. When an image is displayed on the display device 6, the observer wears distance measurement glasses 610. Two markers (markers 611A and 611B) that reflect infrared light are arranged on the distance measurement glasses 610.

When infrared light is emitted from the infrared light emitter 602, the markers 611A and 611B of the distance measurement glasses 610 reflect the infrared light toward the display device 6. The first imager 603L and the second imager 603R capture images of the reflected light and thus generate distance measurement image data. The detector 6b outputs the generated distance measurement image data to the controller 35.

Figure 14:
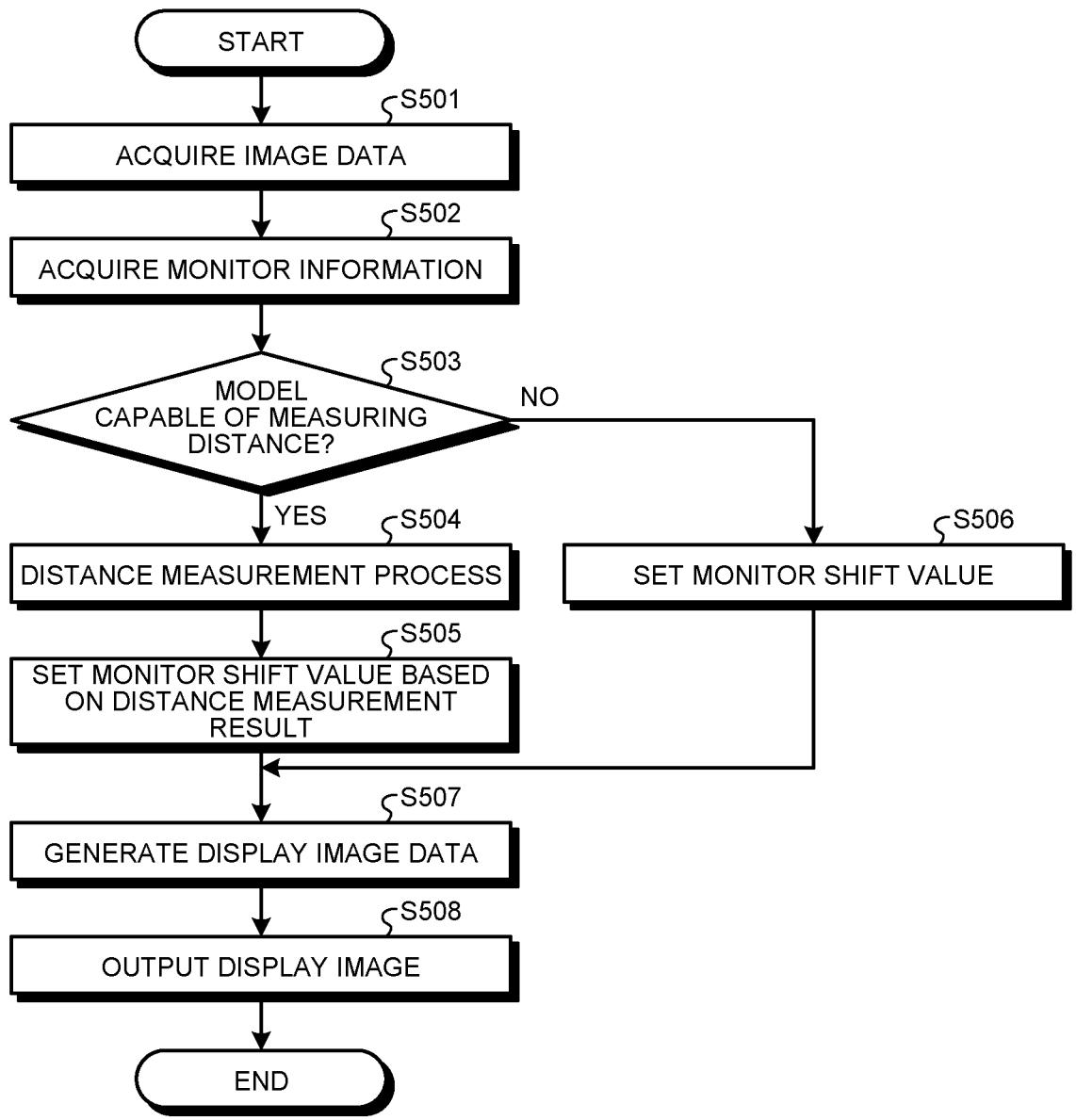
FIG. 14 is a flowchart representing a process that is performed by the endoscope system according to the fourth embodiment of the disclosure.

Image processing performed by the endoscope system 1B will be described. FIG. 14 is a flowchart representing a process that is performed by the endoscope system according to the fourth embodiment of the disclosure. Supposing that each unit operates under the control of the controller 35, description will be given below.

First of all, the processing device 3 acquires image data from the endoscope 2 (step S501). The controller 35 acquires information on the monitor size (monitor information) from a connected display device (the display device 4, the display device 5, or the display device 6) (step S502).

At step S503 following step S502, the controller 35 determines whether the display device is a model capable of measuring a distance from the monitor information. When it is determined that the display device is a model capable of measuring a distance (YES at step S503), the controller 35 moves to step S504.

At step S504, the distance measurement unit 331 acquires distance measurement image data from the display device 6 and measures the distance between the observer and the display device 6.

At step S505 following step S504, the display condition setting unit 33A calculates an appearance monitor size from the distance that is measured at step S504 and the monitor size. Thereafter, the display condition setting unit 33A refers to the monitor shift value determination table that is stored in the storage 36 and sets a monitor shift value corresponding to the appearance monitor size. After setting the monitor shift value, the controller 35 moves to step S507.

On the other hand, at step S503, when it is determine that the display device is not a model capable of measuring a distance (NO at step S503), the controller 35 moves to step S506.

At step S506, as in the first embodiment, the display condition setting unit 33 refers to the monitor shift value setting table that is stored in the storage 36 and sets a monitor shift value corresponding to the monitor size of the connected display device. After setting the monitor shift value, the controller 35 moves to step S507.

At step S507, the signal processor 31 relatively shifts a right-eye image and a left-eye image based on the monitor shift value that is set by the display condition setting unit 33 and performs image processing to generate a signal in a form displayable on the display device 4, thereby generating display image data. The signal processor 31 stores the generated display image data in the frame memory 32.

At step S508 following step S507, the controller 35 causes the connected display device to display a parallax image corresponding to the display image data. The controller 35 sequentially outputs the display image data that is stored in the frame memory 32 to the display device and causes the display device to display the image.

The above-describe fourth embodiment employs the configuration in which a monitor shift value that does not causes divergence is set according to the monitor size in which the observer views the display device (monitor) (appearance monitor size), that is, the display size. According to the fourth embodiment, because the monitor shift value of the parallax image changes according to the distance between the observer and the display device, it is possible to inhibit divergence to the eyes of the observer.

In the fourth embodiment of the disclosure described above, the marker of the distance measurement glasses 610 is not limited to the above-described pattern in which the marker includes two markers, and the marker may include a single or at least three markers. When each of multiple observers wears glasses, patterns of the distance measurement glasses different from one another makes it possible to measure a distance between a specific observer and the display device according to the pattern of the marker. For example, the display condition setting unit 33A measures distances between the observers and the display device and, based on the shortest distance, an apparent display size is calculated and a monitor shift value is set. When the measured distance is smaller than a distance that is preset, the controller 35 may display a two-dimensional image on the display device.

In the first to fourth embodiments, the example in which the parallax image is a line-by-line image is described; however, the parallax image is not limited thereto and the parallax image may be an image with parallax, for example, a side-by-side image in which the left-eye images IME and the right-eye images $IM_R$ are arrayed along the direction of the horizontal line or a top-and-bottom image in which the left-eye images IME and the right-eye images $IM_R$ are arrayed vertically. Furthermore, the parallax image is not limited to a single image and, for example, the left-eye image and the right-eye image may be output alternately as in a frame sequential method.

According to the first to fourth embodiments described above, supposing that a simultaneous illuminating/imaging system in which the imager 244 receives reflected light from illumination light is employed, description is given. Alternatively, a sequential lighting/imaging system in which the illuminator 3a individually and sequentially emits light of bands of wavelength of color components and the imager 244 receives light of each of the color components may be employed.

In the first to fourth embodiments, supposing that the controller 35 functions as an acquisition circuit that acquires left-eye image data and right-eye image data, description is given. Alternatively, the acquisition circuit may be provided independently of the controller 35.

In the first to fourth embodiments, supposing that the illuminator 3a is formed independently of the endoscope 2, description is given. Alternatively, for example, a configuration in which a light source device is arranged in the endoscope 2 by, for example, arranging a semiconductor light source at the distal end of the endoscope 2 may be employed. Furthermore, the endoscope 2 may be given with the function of the processing device 3.

In the first to fourth embodiments described above, supposing that the endoscope system according to the disclosure is the endoscope system 1, 1A or 1B using the flexible endoscope 2 that observes living tissue in a subject, or the like, description is given. Alternatively, an endoscope system using a component obtained by connecting a camera head to an eyepiece of the optical endoscope, such as a ridged endoscope, an industrial endoscope that observes properties of a material, a capsule endoscope, a fiberscope, or an optical scope may be used.

In the above-described embodiments, the endoscope system has been taken as an example and described, and the embodiment is applicable to, for example, the case where a video is output to an electronic view finder (EVF) that is provided in a digital steel camera, or the like.

As described above, the endoscope processor, the display setting method, and the display setting program according to the disclosure are useful in inhibiting divergence to the eyes of an observer when a parallax image is displayed.

According to the disclosure, an effect that it is possible to inhibit divergence to the eyes of an observer when a parallax image is displayed is achieved.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope processor comprising:
   one or more processors comprising hardware, wherein the one or more processors are configured to:
      acquire first image data of a first image and second image data of a second image, the first image and the second image being acquired by an imager of an endoscope;
      acquire display size information on a display size of a display that is connected to the endoscope processor;
      acquire imager property information on a property of the imager of the endoscope;
      based on the display size information and the imager property information acquired, set a monitor shift value by referring to a monitor shift value determination table storing the monitor shift value as corresponding to the display size and the property of the imager; and
      shift, based on the monitor shift value set, the first image and the second image to generate display image data to be output to the display.

2. The endoscope processor according to claim 1, wherein the one or more processors are configured to, based on the display size information, set a display size of a display image, corresponding to the display image data, to be displayed on the display.

3. The endoscope processor according to claim 1, wherein the one or more processors are configured to:
   determine whether the display size of the display is larger than a preset display size;
   in response to determining that the display size is equal to or larger than the preset display size, generate the display image data using one of the first image data and the second image data; and in response to determining that the display size is not equal to or larger than the preset display size, shift, based on the monitory shift value set, the first image and the second image to generate the display image data.

4. The endoscope processor according to claim 1, wherein the one or more processors are configured to:
acquire observation method information on an observation method employed by the endoscope; and
based on the display size information and the observation method information, set the monitor shift value by referring to the monitor shift value determination table storing the monitor shift value as corresponding to the display size and the observation method employed by the endoscope.

5. The endoscope processor according to claim 1, wherein the one or more processors are configured to:
acquire region to be observed information on a region to be observed by the endoscope; and
based on the display size information and the region to be observed information, set the monitor shift value by referring to monitor shift value determination table storing the monitor shift value as corresponding to the display size and the region to be observed by the endoscope.

6. The endoscope processor according to claim 1, wherein the one or more processors are configured to:
acquire measured distance information on a measured distance between the display and an observer who observes an image that is displayed on the display;
calculate a possible display size on the display based on the measured distance information and the display size information, the possible display size being an image display size viewed from the observer;
calculate the monitor shift value based on the possible display size.

7. The endoscope processor according to claim 1, wherein the one or more processors are configured to:
determine whether a display size of a display image that corresponds to the display image data and that is to be displayed on the display is larger than a preset display size; and
in response to determining that the display size of the display image is larger than the preset display size, control the display to display the display image two-dimensionally.

8. A method comprising:
acquiring first image data of a first image and second image data of a second image, the first image and the second image being acquired by an imager of an endoscope;
acquiring display size information on a display size of a display that is connected to an endoscope processor;
acquiring imager property information on a property of the imager of the endoscope;
based on the display size information and the imager property information acquired, setting a monitor shift value by referring to a monitor shift value determination table storing the monitor shift value as corresponding to the display size and the property of the imager; and
shifting, based on the monitor shift value set, the first image and the second image to generate display image data to be output to the display.

9. A non-transitory computer-readable recording medium with an executable program stored thereon, the program causing an endoscope processor to execute:
acquiring first image data of a first image and second image data of a second image, the first image and the second image being acquired by an imager of an endoscope;
acquiring display size information on a display size of a display that is connected to the endoscope processor;
acquiring imager property information on a property of the imager of the endoscope;
based on the display size information and the imager property information acquired, setting a monitor shift value by referring to a monitor shift value determination table storing the monitor shift value as corresponding to the display size and the property of the imager; and
shifting, based on the monitor shift value set, the first image and the second image to generate display image data to be output to the display.

10. An endoscope system comprising:
an endoscope comprising an imager configured to acquire a first image and a second image each having parallax with respect to a same subject; and
one or more processors comprising hardware, wherein the one or more processors are configured to:
acquire first image data of the first image and second image data of the second image;
acquire display size information on a display size of a display that is connected to the endoscope processor;
acquire imager property information on a property of the imager of the endoscope;
based on the display size information and the imager property information acquired, set a monitor shift value by referring to a monitor shift value determination table storing the monitor shift value as corresponding to the display size and the property of the imager; and
shift, based on the monitor shift value set, the first image and the second image to generate display image data to be output to the display.

* * * * *